United States Patent [19]

Bonnet

[11] Patent Number: 4,653,476
[45] Date of Patent: Mar. 31, 1987

[54] INSTRUMENT INSERT FOR A URETERO-RENOSCOPE

[75] Inventor: Ludwig Bonnet, Knittlingen, Fed. Rep. of Germany

[73] Assignee: Richard Wolf GmbH, Fed. Rep. of Germany

[21] Appl. No.: 751,429

[22] Filed: Jul. 3, 1985

[30] Foreign Application Priority Data

Jul. 5, 1984 [DE] Fed. Rep. of Germany ... 8420077[U]

[51] Int. Cl.⁴ ............................................. A61B 1/00
[52] U.S. Cl. ...................................................... 128/4
[58] Field of Search ................................ 128/4, 5, 6, 7

[56] References Cited

U.S. PATENT DOCUMENTS

| | | | |
|---|---|---|---|
| 1,680,490 | 8/1928 | Wappler | 128/7 |
| 1,901,731 | 3/1933 | Buerger | 128/7 |
| 3,561,432 | 2/1971 | Yamaki | 128/6 |
| 3,924,608 | 12/1975 | Mitsui | 128/6 X |
| 4,353,358 | 10/1982 | Emerson | 128/4 |

FOREIGN PATENT DOCUMENTS 2004749 4/1979 United Kingdom .

Primary Examiner—William H. Grieb

[57] ABSTRACT

An instrument insert for a uretero-renoscope comprises a hollow elongate shaft proximally connectible through an outer shaft of the uretero-renoscope and having an optical system extending through it. A steerable deflector device for a flexible auxiliary instrument extending through the insert being provided proximally adjacent the distal objective of the optical system, whereby the distal end of an instrument such as a cannula passing through the insert shaft can be guided from the proximal end of the uretero-renoscope while being viewed through the optical system.

3 Claims, 7 Drawing Figures

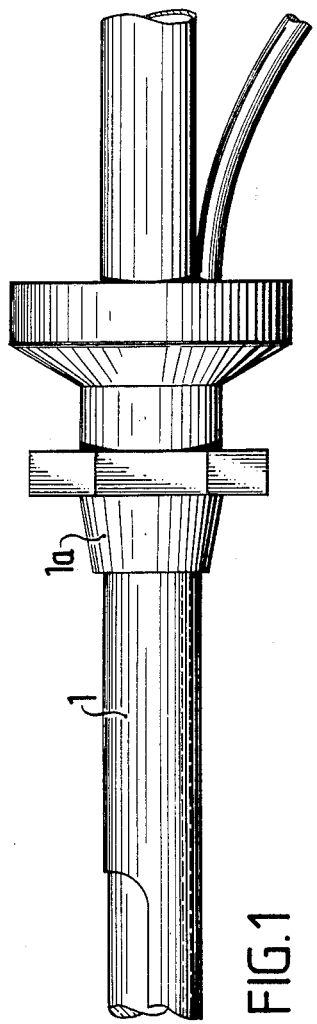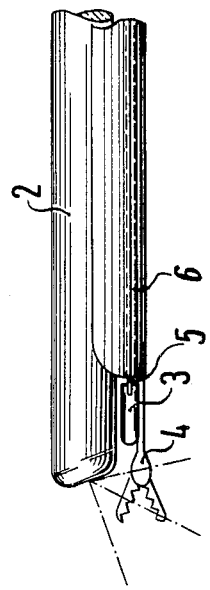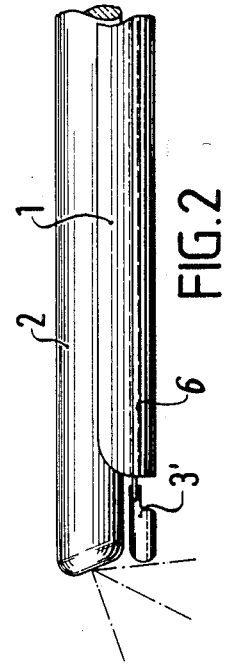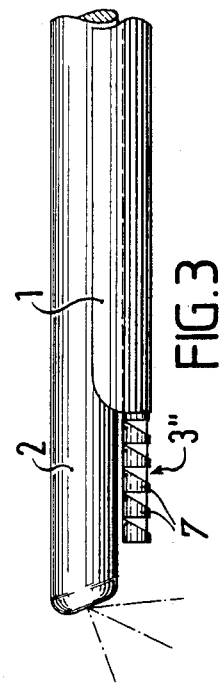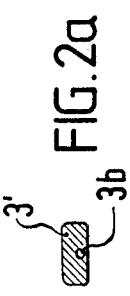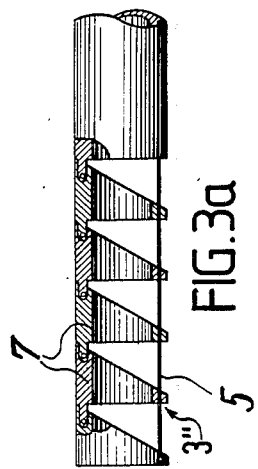

INSTRUMENT INSERT FOR A URETERO-RENOSCOPE

BACKGROUND OF THE INVENTION

1. Field of the Invention

The invention relates to a uretero-renoscope comprising a shaft with a connectible instrument insert extending through it.

2. Description of the Prior Art

For manipulations in the region of the median and lower calyx groups of the kidney, use has been made until now of precurved flexible auxiliary instruments which are not however steerable and cannot retain the momentary position for an extended period without variations. Auxiliary instruments of this kind are usable only to a limited extent for this reason and are very unwieldy to utilise for manipulation.

SUMMARY OF THE INVENTION

It is an object of the invention to provide a ureter renoscope capable of removing stones or tissue from the kidney by means of flexible auxiliary instruments and under visual verification, irrespective of position, in coagulating tumors or the like by means of lasers or high frequency or in being able to guide a cannula in an aimed manner towards the outside of the kidney for establishing a nephrostomy passage under visual verification.

According to the invention, this object is attained in that in the case of the uretero-renoscope referred to above the instrument insert has led through it an optical system and a proximally controllable deflector device for a flexible auxiliary instrument extending through the insert is situated proximally adjacent the objective at the objective end of said optical system.

The deflector device is thus situated at the objective end of the optical system, so that the deflection of the auxiliary instrument may be observed immediately upon emergence from the instrument passage, and is constantly varifiable visually during deviation. The uretero renoscope thus allows aimed manipulation within the kidney, The invention is described in the following with reference to the drawings.

BRIEF DESCRIPTION OF THE DRAWINGS

FIG. 1 is a side view of an instrument insert for a uretero-renoscope,

FIG. 1a is a cross-sectional view through the Albarran lever of FIG. 1,

FIG. 2 is a partial side view of a distal extremity of the instrument insert with a modified Albarran lever illustrated in crosssection in FIG. 2a, FIG. 3 is a partial side view of a distal extremity of the instrument insert with a modified deflector device for auxiliary instruments, FIG. 3a is a partial side view with portions broken away of an end of a deflector device of FIG. 3 in an idle position; and FIG. 3b is a partial side view of an end of the deflector device of FIG. 3 in a deflected position.

DETAILED DESCRIPTION OF THE PREFERRED EMBODIMENTS

The instrument insert 1 shown in FIG. 1 comprises a hollow elongate shaft and is insertable into an outer shaft of a uretero-renoscope which is not illustrated but which engages a tapered surface 1a of the insert. An optical system 2 is introduced into the insert 1, and a passage extends through the insert 1 for leading through an auxiliary instrument 4 which may be deflected at the distal end by a deflector device 3 by means of a proximal control system. The deflector device is situated in front of the objective of the optical system at the objective side and as shown in FIGS. 1 and 1a is an Albarran lever 3 which is provided on the outwardly directed surface with dished depression 3a for reception of the auxiliary instrument 4. The Albarran lever 3 is mounted for angular movement on the distal end of the insert 1, its angular movement being controlled from the proximal end of the insert by means of wires 5 which run through sleeves or channels 6 along each side of the insert 1.

In the embodiment shown in FIG. 1 the Albarran lever 3 controls the angular position of the auxiliary instrument by bearing against it. In the second embodiment shown in FIGS. 2 and 2a, an Albarran lever 3' is provided with a longitudinally extending bore 3b through which the auxiliary instrument 4 passes. The steering mechanism of the Albarran lever may be of known type, for example as disclosed in British Patent Application No. 2004749.

According to FIGS. 3, 3a and 3b, the deflector device 3" comprises annular segments 7 joined in an articulated manner. The deflector device 3" may be moved between a curved configuration as shown in FIG. 3b for the deflection of the traversing auxiliary instrument 4 and the rectilinear setting of FIG. 3a by means of a proximally controllable traction wire 5.

I claim:

1. An instrument insert for a uretero-renoscope comprising a hollow elongate shaft having proximal and distal ends; an optical system passing through said shaft and having an objective adjacent the distal end of said shaft; a passage through said insert for an auxiliary instrument; deflector means being mounted at the distal end of said shaft adjacent the objective of the optical system on the proximal side thereof to steer an instrument passed through said passage, said deflector means comprising an Albarran lever having a longitudinal bore therethrough for the passage of an auxiliary instrument; and means being provided at the proximal end of said insert for steering said deflector means.

2. An uretero-renoscope comprising: a hollow outer rigid tube with a proximal end and a distal end; and an instrument insert received in the outer tube, said insert consisting of a hollow elongate shaft having a proximal end and a distal end, an optical system extending through said shaft and having an objective adjacent the distal end of said shaft, a passage extending through said insert along side of the optical system for receiving an auxiliary instrument, deflector means mounted at the distal end of said shaft adjacent the objective of the optical system on the proximal side thereof to steer an instrument being passed through said passage, said deflector means comprising an Albarran lever having a longitudinal bore therethrough for the passage of an auxiliary instrument, and control means being provided at the proximal end of the shaft and connected to the deflector means for moving said deflector means to steer the instrument.

3. An uretero-renoscope comprising: a hollow outer rigid tube with a proximal end and a distal end; and an instrument insert received in the outer tube, said insert consisting of a hollow elongate shaft having a proximal end and a distal end, an optical system extending through said shaft and having an objective adjacent the distal end of said shaft, a passage extending through said insert along side of the optical system for receiving an auxiliary instrument and including a second tube with a distal end, deflector means mounted at the distal end of said shaft adjacent the objective of the optical system on the proximal side thereof to steer an instrument being passed through said passage, said deflector means comprising annular segments coupled in an articulated manner to define a longitudinal passage for an auxiliary instrument being provided on the distal end of the second tube, and control means being provided at the proximal end of the shaft and connected to the deflector means for moving said deflector means to steer the instrument and said control means including traction wires extending along said shaft for drawing said segments into a curved configuration.

* * * * *